(12) United States Patent
Parkkinen et al.

(10) Patent No.: US 6,326,473 B1
(45) Date of Patent: Dec. 4, 2001

(54) PHARMACEUTICAL PREPARATIONS

(75) Inventors: Jaakko Parkkinen, Espoo; Leni von Bonsdorff-Lindeberg, Kauniainen, both of (FI)

(73) Assignee: Suomen Punainen Risti Veripalvelu, Helsinki (FI)

( * ) Notice: Subject to any disclaimer, the term of this patent is extended or adjusted under 35 U.S.C. 154(b) by 0 days.

(21) Appl. No.: 09/223,178

(22) Filed: Dec. 30, 1998

(51) Int. Cl.$^7$ .............................. C07K 1/00; C07K 14/00; C07K 17/00; A61K 35/14; A61K 38/16

(52) U.S. Cl. ..................... 530/394; 530/350; 530/380; 530/394; 530/395; 530/412; 530/416; 514/12; 514/8

(58) Field of Search .................. 514/8, 12; 530/380, 530/394, 395, 412, 416, 350

(56) References Cited

U.S. PATENT DOCUMENTS

| | | | |
|---|---|---|---|
| 5,041,537 | 8/1991 | Bethke et al. | 530/394 |
| 5,252,715 | 10/1993 | Haupt | 530/394 |
| 5,744,586 | 4/1998 | Rolf et al. | 530/394 |

FOREIGN PATENT DOCUMENTS 9749414   12/1997   (WO) .

OTHER PUBLICATIONS

Robbins–Browne, et al., *Infection and Immunity*, vol. 47, No. 3, pp. 774–779 (Mar. 1985).
Beare et al., *The Lancet*, vol. 347, pp. 342–343 (Feb. 1996).
Ward et al., *J. Trauma*, vol. 41, No. 2, pp. 356–364 (Aug. 1996).
Rigal et al., *Biotechnology of Plasma Proteins, Colloque INSERM*, vol. 175, pp. 107–114 (1989).

*Primary Examiner*—Karen Cochrane Carlson
*Assistant Examiner*—Chih-Min Kam
(74) *Attorney, Agent, or Firm*—Birch, Stewart, Kolasch & Birch, LLP

(57) ABSTRACT

The present invention relates to pharmaceutical compositions of transferrin and to the manufacture of such preparations. The present invention concerns specifically a pharmaceutical composition of apotransferrin, the iron-free form of transferrin, wherein the composition has at least 90% of the theoretical iron binding capacity of iron-free transferrin, contains less than 3% transferrin dimers and no detectable transferrin polymers or aggregates, and has an iron-saturation of less than 5%. The pharmaceutical apotransferrin composition of this invention effectively binds non-transferrin-bound-iron to a harmless form when administered as an intravenous injection or infusion to patients. The pharmaceutical composition of this invention does not contain viruses, denatured forms of transferrin or other harmful components.

3 Claims, 5 Drawing Sheets

PHARMACEUTICAL PREPARATIONS

BACKGROUND OF THE INVENTION

1. Field of the Invention

The present invention relates to pharmaceutical compositions of transferrin and to the manufacture of such preparations. The present invention further relates to the use of the pharmaceutical compositions in the prevention of harmful effects of non-trasferrin-bound iron in patients.

2. Description of Related Art

Transferrin is a protein which transports iron in blood plasma and extracellular fluid in tissues. Transferrin binds two ferric ($Fe^{3-}$) ions per molecule with high affinity, and normally all iron in plasma is bound to transferrin. Apo-transferrin is the iron-free form of transferrin. As used in the present context, the term "transferrin" is used for designating all forms of transferrin irrespective of their iron content.

In certain pathological conditions the concentration of iron exceeds the iron binding capacity of transferrin, and non-transferrin-bound iron (in the following abbreviated "NTBI") can be detected in serum samples of the patients. Such pathological conditions include malignant neoplastic diseases, such as leukemias. The appearance of NTBI is particularly common during cytotoxic chemotherapy of malignant diseases (reviewed in Beare and Steward, Lancet 347,342–343, 1996).

NTBI catalyses the generation of highly reactive hydroxyl radicals, and it is proposed that NTBI plays a pathogenetic role in tissue damage caused by cytotoxic therapy. Therefore, it has been suggested in the prior art that iron-chelating agents should be administered to patients undergoing cytotoxic chemotherapy in order to prevent the harmful effects of NTBI (Beare and Steward, Lancet 347, 342–343, 1996). Dexrazone (ICRF187, ADR–529), a synthetic iron chelator, has been shown to reduce anthracycline-induced cardiotoxicity in animal studies and in the treatment of women with advanced breast cancer. Another iron chelator, desferrioxamine, reduced experimental bleomycin-induced pulmonary fibrosis, and it was also suggested to be advantageous in the chemotherapy of advanced neuroblastoma (Beare and Steward, Lancet 347, 342–343, 1996).

A disadvantage in the administration of synthetic chelators is that they cause severe adverse effects, such as myelosuppression (Beare and Steward, Lancet 347, 342–343, 1996). Another drawback is that the chelated iron can be utilized by bacteria, and chelation therapy may predispose the patient to infections (Robins-Browne and Prpic, Infect Immun 47, 774–779, 1985). This is especially undesirable in patients undergoing high dose cytotoxic therapy for maligant diseases, as these patients typically suffer from septic infections caused by bacteria and fungi. Septic infections caused by multiresistant bacteria are an important cause of mortality in these patients. As free iron in general promotes the growth of bacteria and fungi (reviewed in Ward et al., J Trauma 41, 356–364, 1996), the binding of NTBI in patients to a form which could not be utilized by bacteria and fungi would be valuable in the treatment of patients undergoing cytotoxic therapy for malignant diseases.

Theoretically, administration of purified transferrin might have beneficial effects in patients by binding extracellular NTBI to a harmless form. Therapeutic use of transferrin has been studied before in three patients undergoing myeloablative chemotherapy and bone marrow transplantation (Rigal et al., Biotechnology of plasma proteins, Colleque INSERM 175, 107–114, 1989). Two of the three patients developed acute renal failure, which may have been associated with the administration of the transferrin preparation. This study did not demonstrate efficacy of the transferrin preparation in the binding of NTBI in the patients or any other benefit but rather suggest that the therapeutic use of transferrin may not be safe.

A transferrin product that could be safely given to patients should evidently be free of viruses and other infectious agents and potentially harmful impurities. A few possibilities have been proposed for the manufacture of virus-safe transferrin products. U.S. Pat. No. 5,252,715 describes a process for the preparation of a pasteurized human plasma transferrin. A purified transferrin solution was pasteurized in the presence of a complexing agent, and the complexing agent was removed with the bound iron. The therapeutic use of transferrin in the rare cases of atransferrin anemia (congenital transferrin defiency) or use as growth factor was suggested.

The particular problem of U.S. Pat. No. 5,252,715 is the generation of transferrin aggregates as a result of the heat treatment used as a virus inactivation step. These problems are also discussed in U.S. Pat. No. 5,041,537. Even in the favourable conditions described in U.S. Pat. No. 5,252,715 small quantities of transferrin aggregates are said to be formed, which the inventors recommend to be removed by adsorption with aluminium hydroxide. The use of aluminium compounds is not desirable, as the serious adverse effects that were associated with the earlier administration of transferrin preparation to patients were suggested to be caused by the high aluminium content of the product (Rigal et al., Biotechnology of plasma proteins, Colleque INSERM 175, 107–114, 1989). The inventors of U.S. Pat. No. 5,252,715 also mention anion-exhange chromatography as a means of reducing the amount of transferrin aggregates. However, even under the favorable conditions, the purified transferrin product was said to contain 2–5% aggregates, which is nondesirable as aggregated transferrin is denaturated, biologically inactive and potentionally harmful. Furthermore, the use of heat treatment as the only virus elimination step in the manufacturing process may not assure safety against physicochemically resistant infectious agents, such as parvoviruses and agents causing transmissible spongiform encephalopathies ("prions").

U.S. Pat. No. 5,041,537 describes another process for the manufacture of virus-inactivated transferrin from human plasma. The process comprises UV-treatment in the presence of β-propiolactone or treatment with tri-(n-butyl) phosphate and a detergent as a virus inactivation step. The occurrence of viral transmission with plasma-derived protein pharmaceuticals treated with a single virus elimination step has resulted in a consensus that multiple virus elimination steps addressing both enveloped and non-enveloped viruses must be incorporated in the processing of plasma-derived proteins. Therefore, the procedure described in U.S. Pat. No. 5,041,537 does not result in a virus-safe product according to current state of the art. The iron-binding capacity of the product was said to be about 80%, which is not satisfactory for the therapeutic use of transferrin described in the present invention.

In conclusion, the prior art does not provide pharmaceutical compositions of transferrin which could be safely and effectively used for the binding of extracellular NTBI in patients to a harmless form. Neither does the prior art provide any other safe and effective method for the prevention of the harmful effects of NTBI in patients. Therefore, the present invention aims at providing a therapeutically useful transferrin composition which lacks the disadvantage of the known preparations. Further, the present invention provides an effective method for the prevention of the harmful effects of NTBI in patients.

SUMMARY OF THE INVENTION

It is an object of the present invention to provide a pharmaceutical composition comprising virus-safe apotransferrin, which has high iron binding capacity and lacks aggregated and otherwise denaturated proteins and other potentially harmful impurities, and which can be safely administrated to patients for the prevention of the harmful effects of NTBI.

It is another object of the present invention to provide a novel method for preparing and purifying apotransferrin and for formulating it into a pharmaceutically useful preparation suitable for intravenous infusion.

A third object of the present invention is to provide a process for the manufacture of safe and effective pharmaceutical apotransferrin compositions, which can be administered to patients undergoing cytotoxic therapy to prevent the harmful effects of NTBI.

It is a fourth object of the present invention to provide a method for preventing the harmful effects of NTBI in patients.

These and other objects, together with the advantages thereof over the known pharmaceutical compositions, manufacturing processes and therapeutic methods, which shall become apparent from specification which follows, are accomplished by the invention as hereinafter described and claimed.

The invention is based on the finding that a pharmaceutical composition comprising effective amount of pure and virus-safe transferrin having high iron binding capacity can be safely administered to patients undergoing cytotoxic treatment, and thereby prevent the harmful effects of NTBI in the patients.

Further, the invention is based on the finding that such pharmaceutical compositions of transferrin can be manufactured from human plasma by recovering transferrin from a Cohn fraction IV, by prepurifying the transferrin and then subjecting the transferrin to a combination of a solvent/detergent treatment step, an anion exchange chromatography step and a virus filtration step. The two virus inactivation/removal steps are carried out under conditions, which cause substantially no protein denaturation. Optionally the iron concentration of the transferrin product can be modified during the isolation process to provide iron-containing transferrin or essentially iron-free transferrin (apotransferrin).

The present invention also provides a particularly advantageous process for preparing an apotransferrin composition comprising solubilizing transferrin from Cohn Fraction IV under conditions, which maintain the transferrin in the iron-free apotransferrin form in aqueous solution. The apotransferrin is then purified by a combination of cation exchange chromatography and anion exchange chromatography, and by eliminating viruses and other physico-chemically resistant infectious agents by subjecting the apotransferrin preparation to at least two virus inactivation/removal steps under conditions, which cause substantially no protein denaturation. As a result of the above-described process steps it is possible to obtain a pharmaceutical composition of apotransferrin, wherein the purity of apotransferrin is more than 98% and wherein the composition contains less the 3% of transferrin dimers and no detectable transferrin polymers or aggregates. "No detectable" amount of transferrin polymers and aggregates means that no peak is seen in size exclusion liquid chromatography, the lower detection limit of the method being about 1%, preferably less than 0.5%. The iron-saturation of the apotransferrin composition is less that 5%, preferably less than 2%, and it has more than 90% of the theoretical iron binding capacity of iron-free transferrin when studied by iron titration. The apotransferrin composition is suitable for intravenous infusion As apparent to a person skilled in the art, the apotransferrin compositions of the present invention may contain various known excipients and stabilizers, such as albumin, sugars and polyols. The above mentioned limits for purity, iron-saturation and iron binding capacity are calculated from the apotransferrin portion of the composition.

As the below test results show, the novel apotransferrin composition provides excellent results when administrated to patients undergoing cytotoxic therapy.

Considerable advantages are obtained with the present invention. Thus, the manufacturing process according to the invention provides highly purified and virus-safe apotransferrin, which retains its full iron-binding capacity. The process has the capacity to eliminate viruses and other infectious agents with diverse physico-chemical properties. The apotransferrin is produced with a minimum number of process steps, which makes it possible to use the invention for large scale, economical manufacturing of the product.

Importantly, the pharmaceutical apotransferrin composition of this invention effectively binds NTBI to a harmless form when administered as an intravenous injection or infusion to patients. According to the present invention, the ability of the patient's blood plasma to resist the growth of multiresistant bacteria can be restored by giving an effective amount of the pharmaceutical composition. The pharmaceutical composition of this invention does not contain potentially harmful viruses, denaturated forms of transferrin or other harmful components, and it can be safely administered as an intravenous injection or infusion even to critically ill patients. By giving a pharmaceutical apotransferrin preparation of this invention to patients undergoing high dose cytotoxic therapy. NTBI can be bound to a form, which can be later utilized by the recovering bone marrow in the formation of blood cells. Accordingly, the invention is directed to the therapeutic use of apotransferrin in patients undergoing cytotoxic therapy and in other clinical conditions, in which serum transferrin is saturated with iron and there is NTBI in serum.

Next the invention will be examined more closely with the aid of a detailed description and a number of working example.

DETAILED DESCRIPTION OF THE INVENTION

Figure 1:
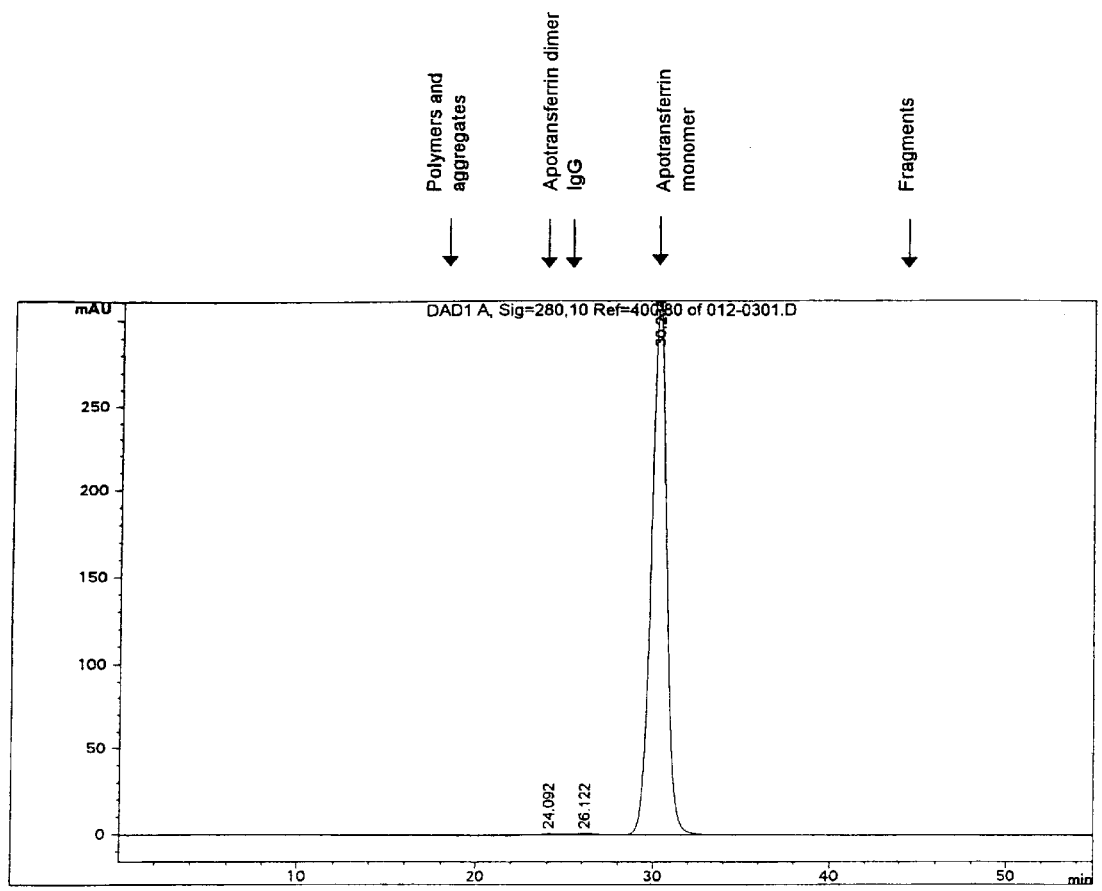
FIG. 1 shows a size exclusion liquid chromatogram for a composition according to the present invention, the arrows indicating the retention times of different molecular species.

Manufacture of Virus-Safe-Pure Apotransferrin with High-Iron Binding Capacity The present invention comprises two process alternatives. The second, preferred embodiment differs from the first one in the sense that the starting material, the Cohn fraction IV, is dissolved at a pH in the acid region in order to keep transferrin in iron-free form, in which it mainly exists in Cohn fraction IV paste. In the first process higher pH values can be used in the prepurification steps. Further, in the first embodiment a buffer exchange step performed by ultrafiltration may become necessary before solvent treatment and anion exchange chromatography.

According to a first embodiment of the present invention, the process is started from a Cohn fraction IV paste, which is dissolved in water or aqueous buffer. Depending on the intended therapeutic use, due care is taken that starting material has a sufficiently low titer of the non-enveloped parvovirus B19 (cf. below). Transferrin is subjected to a partial purification by methods known in the art (cf. for example U.S. Pat. No. 3,850,903 and the above mentioned U.S. Pat. No. 5,041,537). Then the partially purified transferrin is subjected to a virus inactivation treatment with an organic solvent optionally together with a detergent (cf. below) The treated transferrin is recovered and subjected to anion exchange chromatography on an ion exchanger and then eluted from the ion exchanger. At this stage, the iron content of the eluted transferrin can be modified by adding iron or removing it by decreasing pH and optionally adding a chelating agent. The eluate is, in optional order, then concentrated and subjected to virus removal filtration. By the process a virus-safe transferrin solution retaining its iron-binding capacity can be obtained.

According to a preferred embodiment of this invention the preparation of virus-safe human plasma apotransferrin is likewise started from Cohn fraction IV paste, which is dissolved in water. However, to prevent the binding of iron to transferrin, pH is kept below 6.0 during dissolution and chelating agent is added to bind iron. Apotransferrin is prepurified and concentrated by binding it to a cation exchange chromatography resin and eluting it by raising the pH. The prepurified apotransferrin is virus inactivated by using an organic solvent and a detergent. Apotransferrin is bound to an anion exchange chromatography resin, and eluted by increasing salt concentration. The protein concentration and formulation of the product is adjusted by ultrafiltration. The product is filtered using a virus removal filter. The preparation is sterilized by filtration and filled aseptically into containers. The product can be stored either in liquid state or can be lyophilized.

The combination of two different ion exchange chromatography steps with the solvent/detergent treatment and the virus filtration will improve the virus-safety of the apotransferrin composition.

In a particularly preferred embodiment of the latter process alternative, Cohn fraction IV paste is dissolved in water or in a buffer solution with low ionic strength (<5 mS/cm). The pH of the solution is held below 6.0, which does not require pH adjustment, when a typical Cohn fraction IV is used. A preferable pH range is 5.4–5.9. A chelating agent, e.g. ethylenediamine-tetraacetic acid (EDTA), or salts thereof, is added to the solution to a concentration of 1 to 10 mmol/l. The solution is clarified by filtration using a depth filter, and the obtained clear solution is collected. The partial purification and concentration of apotransferrin can be obtained by adsorbing it to a cation exchange resin equilibrated at pH 5.5–6.0 with buffer of ionic strength below 5 mS/cm. The functional group of the cation exchange resin is either carboxymethyl (CM) or sulphonyl, most preferably sulphopropyl (SP) such as in SP Sepharose (Amersham Pharmacia Biotech). Apotransferrin is eluted from the column using a buffer with a pH of 7.0–7.5. The eluate is collected and the pH of the eluate is adjusted to 7.0–7.5. The use of pH-dependent elution makes it possible to obtain a solution with low ionic strength (<5 mS/cm) suitable for the following anion exchange chormatography without buffer exchange. The preferred elution buffer contains 40 mmol/l Tris-HCl, pH 7.5.

In the process alternatives of the invention, the partially purified (apo) transferrin preparation is treated with an organic solvent, such as tri-(n-butyl) phosphate, either with or without a detergent to inactivate enveloped viruses. S/D treatments are disclosed in the art, in particular in U.S. Pat. Nos. 4,540,573, 4,764,369 and 4,820,805 the contents of which are herewith incorporated by reference. The organic solvent is preferably selected from dialkylphosphates and trialkylphosphates having alky groups which contain 1 to 10 carbon atoms. Examples of trialkylphosphates are tri-(n-butyl) phosphate, tri-(t-butyl) phosphate, tri-(n-hexyl) phosphate and tri-(2-ethylhexyl) phosphate. The concentration of the solvent is in the range of 0.01 g/l to 100 g/l, preferably about 0.1 g/l to about 10 g/l, a typical concentration of tri-(n-butyl)-phosphate being about 0.3%. The solvent can be used together with a non-toxic detergent, which is capable of enhancing the effectiveness of the solvent. Such substances are exemplified by non-ionic surfactants, e.g. oxyethylated alkyl phenols, polyoxyethylene sorbitan fatty acid esters, polyoxyethylene alcohols and sodium deoxycholate. The amount of the detergent is in the range of 0.001 to 10%, preferably about 0.01 to 1.5%. Typically, the detergent comprises 1% polysorbate 80 (Tween 80), 1% Triton X-100 or 0.2% sodium deoxycholate. S/D substances may be used even at higher concentrations, such as 2% tri-n(n-butyl)phosphate without a detergent. The treatment time may be 4–50 h, and the temperature 24–30° C.

In the preferred conditions of the present invention the organic solvent is 0.3% of tri-n-butyl) phosphate, the detergent is 1% polysorbate 80 or 1% Triton X-100, and the incubation is carried out for 6–10 h at 24–30° C.

The virus-inactivated (apo) transferrin preparation is adsorbed to an anion exchange resin equilibrated with a buffer at pH 7.5. The functional group of the anion exchange resin can be selected from diethylaminoethyl (DEAE) and quaternary ammonium (Q), most preferably quaternary ammonium, such as in Q Sepharose (Amersham Pharmacia Biotech), is used. The apotransferrin is eluted with a buffer containing 60–100 mmol/l NaCl, most preferably a buffer containing 40 mmol/l Tris-HCl, 85 mmol/l NaCl, pH 7.5.

In a preferred formulation according to the present invention the pH of the pure apotransferrin is adjusted to 5–7.5, preferably 5.8–7.2. The elution buffer is exchanged to a formulation solution suitable for intravenous infusion, such as 100–150 mmol/l NaCl, and the product is concentrated to a protein concentration of 20–100 g/l by ultrafiltration. Optionally, in order to assure a very low iron saturation of the transferrin preparation (less than 1%), the pH of the eluate can be decreased below 5.0 and a chelating agent, such as EDTA, can be added before ultrafiltration.

The pure apotransferrin solution is subjected to virus filtration before or after ultrafiltration using a specific virus removal filter, preferably with a pore size of 10 to 40, in particular 10–20 nm. The apotransferrin solution is sterilized by filtration and filled aseptically into sterile containers. Lyophilization can be optionally done but is not required, since the liquid formulation is stable and ready for infusion without preceding reconstitution.

Pharmaceutical Compositions of Transferrin with High-Iron Binding Capacity

Figure 2:
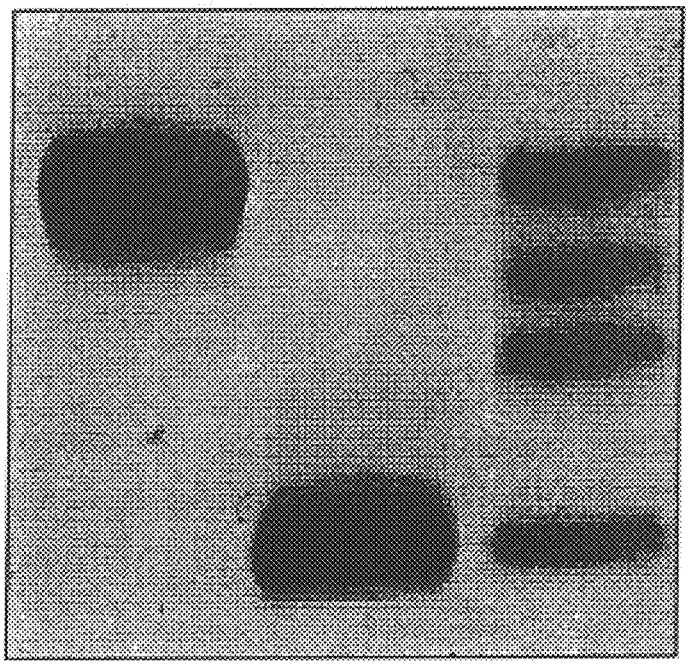
FIG. 2 shows a urea-polyacrylamide gel electrophoresis before (lane 1) and after (lane 2) iron saturation of the pure apotransferrin preparation having high iron binding capacity, the standard containing all iron forms of transferrin was run in lane 3.

By the present invention, a pharmaceutical composition of apotransferrin can be produced having a purity of more than 98% and containing less than 3%, preferably less than 2%, dimers and no detectable polymers or aggregates (cf FIG. 1). The purity can be studied by cellulose acetate and sodium dodecyl sulphate-polyacrylamide gel electrophoresis and molecular size distribution by size exclusion liquid chromatography. The lack of denaturated protein forms can be demonstrated by urea-polyacrylamide gel electrophoresis before and after iron saturation of the preparation, as shown in FIG. 2 and Example 2.

Figure 3:
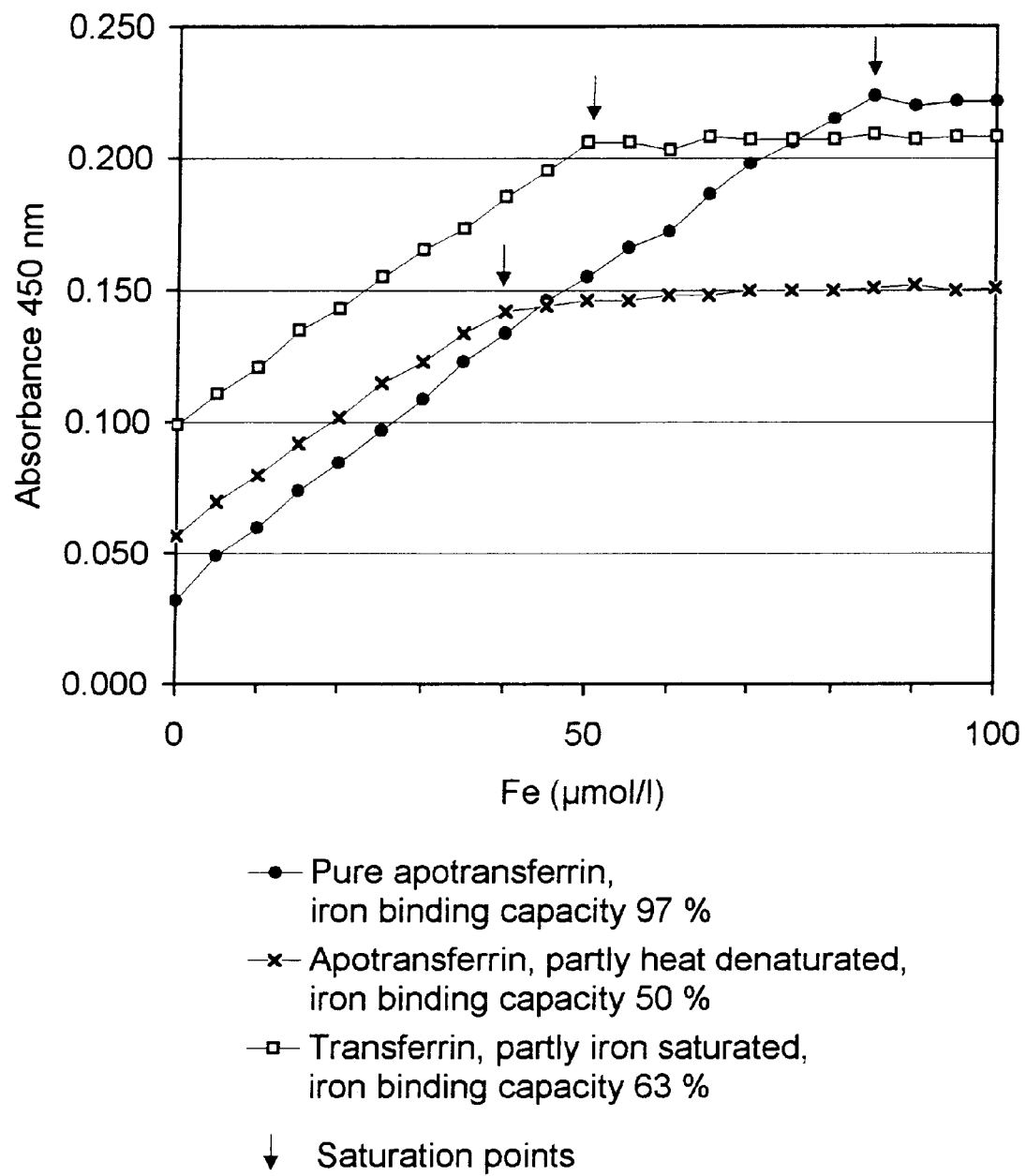
FIG. 3 shows the iron-binding capacity of different transferrin preparations as determined by adding increasing amounts of ferric iron to the transferrin preparations and monitoring iron binding by absorbance at 450 nm.

The iron-saturation of transferrin in the pharmaceutical composition is less than 5% (preferably less than 2%), and it has more than 90% of the theoretical iron binding capacity of iron-free transferrin. Iron binding capacity is determined by titration with iron nitrilotriacetic acid as shown in FIG. 3 and Example 2.

The present apotransferrin preparations are truly virus-safe in the sense that they are free from infectious, potentially harmful viruses. An essential part in manufacturing of a virus safe product is to ensure that the load of potentially harmful viruses in the starting material does not exceed the capacity of the manufacturing process to eliminate potential residual viruses in the starting material. Particularly, parvovirus B19 may be present in human plasma pools at levels of up to $10^8$/ml, and it is resistant to most virus inactivation procedures including solvent/detergent treatment. A single virus filtration step may remove infectious parvovirus at least by $10^5$ fold, but due to the potentially very high virus load this will not result in freedom of parvovirus in the product. On the other hand, as parvovirus is not considered especially harmful for most recipients of plasma products, e.g. hemophilia patients, many plasma products which may possibly contain parvovirus and which therefore are not "substantially virus-free" can be regarded as essentially virus-safe. Even albumin products and recombinant coagulation products, which are considered as essentially virus-safe, have been shown to contain parvovirus by PCR. However, if a plasma product is to be used for a patient population for which parvovirus infection is potentially harmful, such as stem cell transplantation patients receiving apotransferrin according to the present invention, then the product must be produced from plasma which has been tested for parvovirus to ensure that the virus load will not exceed the capacity of the manufacturing process to eliminate it. In practice the level of parvovirus B19 in the starting plasma should be less than $10^3$/ml, preferably less than $10^2$/ml. Parvovirus titer may be determined as genome equivalents by PCR or virus particles by using generally known techniques.

Alternatively, the manufacturing process must contain several steps which together effectively remove or inactivate parvovirus (preferably at least $10^{10}$ fold) to eliminate even a high parvovirus load in the starting plasma. Another alternative to restrict potential virus load in the starting material is to use recombinant DNA technology in the production of transferrin.

The pharmaceutical composition of the present invention is suitable for intravenous infusion or injection. The concentration of apotransferrin in the solution is 1–200 g/l, preferably about 20–100 g/l, to allow the administration of effective amounts of apotransferrin without causing excessive volume load to the patients. The preparation may be lyophilized and reconstituted before administration or it may be stored as a solution ready for administration. The pH of the solution product is 5 to 7.5, preferably about 5.8–7.2, which is a preferential for the stability of the liquid product. The osmolality of the solution is preferentially at least 240 mosmol/l, which can be achieved by adding sodium chloride and/or organic molecules, such as sugars, polyols or amino acids. Pharmaceutically acceptable excipients and stabilizers, such as albumin, sugars and various polyols, can be added to the compositions, typically in amounts ranging from 0 to 50 wt-% of the amount of the active protein. The liquid formulation is preferred, as it is economical to produce and is ready for administration without reconstitution.

Methods of Therapy

The transferrin composition according to the present invention is therapeutically useful in pathological conditions characterized by the presence of NTBI in the patient serum. The administration of the pharmaceutical composition is particularly useful during cytotoxic therapy of malignant diseases, such as cytotoxic chemotherapy and/or cytotoxic radiation therapy, and myeloablative therapy in association of stem cell transplantation.

The pharmaceutical composition is administered as an intravenous injection or infusion to the patients. Effective doses of apotransferrin vary from 20 to 500 mg/kg per day, preferably from 50 to 250 mg/kg per day, depending on the clinical condition. The dose may be reduced during repeated administration.

The apotransferrin of the pharmaceutical composition binds extracellular NTBI to a harmless form and prevents the harmful effects of NTBI in patients. These harmful effects comprise toxic effects caused by free radical generated by NTBI, including mucositis and liver and heart injuries, and the microbial growth-promoting effects of NTBI in patients' plasma and extracellular fluids. Further, the apotransferrin binds NTBI in a form which can be utilized by the recovering bone marrow. Thus, the pharmaceutical composition decreases organ toxicity associated with chemotherapy and radiation therapy, and increases the resistance of the patients against bacterial and fungal infections. Also, it promotes the recovering of the bone marrow after stem cell transplantation.

It is noteworthy that the administration of the apotransferrin composition increases serum iron concentration in contrast what has been suggested before. Ward et. al. (J Trauma 41, 356–364, 1996) suggested that if administration of purified apotransferrin to patients with acute myeloid leukemia could reduce high serum iron to normal levels, the resistance of leukemia patients to infection might be increased. The present invention indicates that the mechanism being bacterial growth inhibition by the transferrin composition is the binding of NTBI to a harmful form and not a decrease of high serum iron level.

The safety and efficacy of the described pharmaceutical composition in the binding of NTBI to a harmless form when administered to patients is demonstrated in Example 3.

Transferrin Produced by Recombinant DNA Technology

The pharmaceutical apotransferrin composition can according to the present invention be prepared from human plasma transferrin or human transferrin produced by recombinant DNA technology. The cloning and sequencing of the cDNA encoding the human transferrin protein has been described in U.S. Pat. No. 5,026,651. This cDNA sequence can be transfected to a suitable host for the mass production of the recombinant protein, such as cultured animal or yeast cells or transgenic animals. The recombinant protein can be purified using a suitable combination of techniques, including those described in the present invention, to obtain a pure apotransferrin preparation, and a pharmaceutical composition according to the present invention can be manufactured from the purified recombinant protein. A composition of the recombinant transferrin according to the specifications of the present invention can be administrated to patients for the prevention of the harmful effects of NTBI identically with the composition of the plasma-derived apotransferrin.

The following non-limiting examples illustrate the invention:

Analytical Methods used in the Examples

SDS-PAGE

Sodium dodecyl sulphate-polyacrylamide gel electrophoresis (SDS-PAGE) was carried out using 10% gets under non-reducing conditions. The gels were stained using silver staining.

Cellulose Acetate Electrophoresis

The determination was carried out according to the method described in Ph. Eur.3rd. Ed. 2.2.31 (1997).

Molecular Size Distribution

The determination was carried out by size exclusion liquid chromatography according to the method described in Ph. Eur. 3rd Ed. 2.2.29 (1997) and 2.2.30 (1997) for human albumin. An example of a chromatogram is shown in FIG. 1.

Urea-PAGE

Urea-polyacrylamide gel electrophoresis (urea-PAGE) was carried out as described before (Williams et al., Biochem J 173, 535–542) using 6% gels with 6 M urea. The gels were stained with Coomassie Blue. An example of a urea-PAGE gel is shown in FIG. 2.

Iron Binding Capacity

Iron binding capacity of transferrin was determined by with ferric nitrilotriacetic acid as described before (Welch and Skinner, Comp Biochem Physiol 93B, 417–424, 1989). Iron binding to transferrin was monitored by following the increase in absorbance at 450 nm. The iron binding capacity was calculated using Equation (1):

$$\text{Iron binding capacity (\%)} = \frac{[\text{Fe-titrated}]}{[\text{Fe-theoretical}]} \times 100\% \tag{1}$$

Wherein

[Fe-titrated]=Amount of iron added to saturate transferrin in the titration (mol/l)

[Fe-theoretical]=Amount of iron required to theoretically saturate transferrin iron (mol/l)

[Fe-theoretical] was calculated according to Equation (2):

$$[\text{Fe-theoretical}] = \frac{\text{Protein content (g/l)} \times 2}{M_{transferrin}} \tag{2}$$

Wherein

Protein content was measured using biuret method $M_{transferrin}$=molecular weight of transferrin 79570 (g/mol)

Results of the iron binding capacity determination for different transferrin preparation are shown in FIG. 3.

Total Protein

Total protein was measured according to the biuret method using human serum albumin as a standard (Total Protein Standard, Finish Red Cross Blood Transfusion Service. Helsinki, Finland).

Prekallilcrein activator

Prekallikrein activator activity was measured according to Ph. Eur. 3rd Ed. 2.6.15 (1997).

Iron Saturation

The iron saturation of transferrin was determined by measuring the iron content of transferrin using the ferrozine method ("Iron without deproteinization"-kit, Boehringer Mannheim Diagnostics GmbH) and calculating the iron saturation of transferrin according to Equation (3):

$$\text{Iron saturation \%} = \frac{[\text{Fe-transferrin}]}{[\text{Fe-theoretical}]} \times 100\% \tag{3}$$

Wherein

[Fe-transferrin]=The measured iron concentration (mol/l)

[Fe-theoretical]=Amount of iron required to theoretically saturate transferrin iron (mol/l), see Equation (2)

BDJ-Assay

Non-transferrin bound iron in serum samples was determined using the bleomycin detectable iron (BDI) assay as described before (Evans and Halliwell, Meth Enzymol 233, 82–92, 1994).

Bacterial Growth Index

Figure 5:
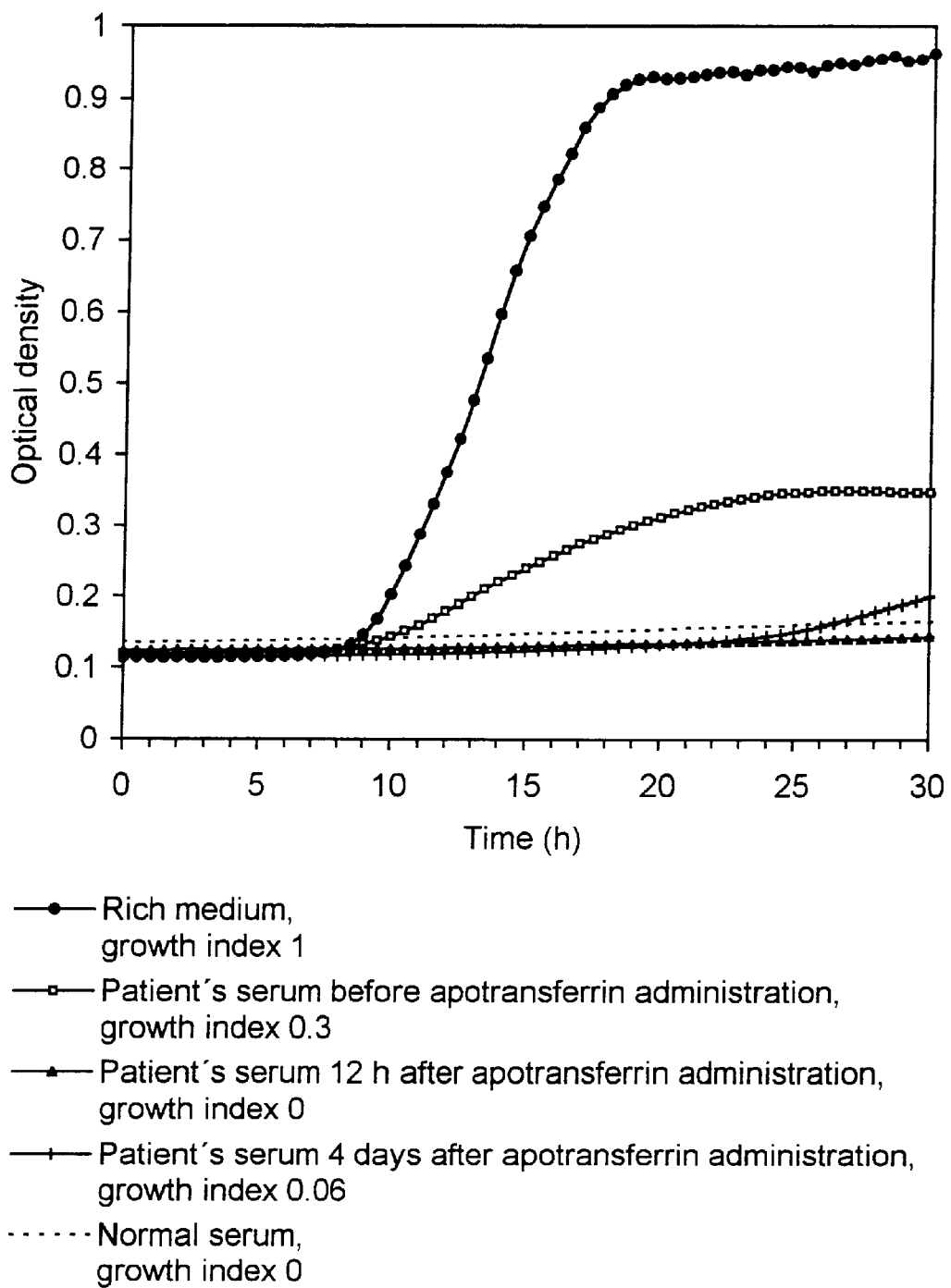
FIG. 5 shows the growth of *Staphylococcus epidermidis* in serum samples before and after administration of a single injection (100 mg/kg.) of a pharmaceutical apotransferrin composition according to the present invention to a patient undergoing high-dose cytotoxic therapy. Growth in normal serum and rich culture medium are shown for reference.

The growth index was calculated from the growth curves of serum samples which had been inoculated with bacteria. The serum samples were diluted 1/5 in a buffered medium with very low iron concentration (Reeves et al. J Bacteriol 154, 324–329, 1983) in order to avoid pH changes during growth. An inoculum of a multiresistant strain of *Staphylococcus epidermidis* isolated from a patient with a septic infection was added to the samples and they were incubated at 37° C. with shaking. The growth was monitored as optical density (absorbance) units. Normal human serum and rich broth (Trypcase-soy broth, bioMéieux) were used as a controls. Typical growth curves are shown in FIG. 5.

The growth index was calculated according to Equation 4:

$$\text{Growth index} = \frac{\mu/\text{lag of patients serum}}{\mu/\text{lag of rich broth}} \quad (4)$$

Wherein $\mu$=specific growth rate during exponential growth phase ($h^{-1}$)

lag=Lag phase of growth (h)

If no growth was detected, the growth index was 0.

EXAMPLE 1

This Example describes how an iron-depleted virus-safe transferrin preparation can be produced from human plasma.

The starting material was approximately 20 kg of Cohn fraction IV paste, which was dissolved in 250 L of water for injection. The protein solution was recovered by plate and frame filtration, using filter aid. Approximately 300 kg of solution was obtained after displacement of the filter unit. EDTA was added to the solution to a concentration of 5 mmol/l. The solution was applied to a chromatography column packed with SP Sepharose (Amersham Pharmacia, Sweden) gel and pre-equilibrated with 40 mmol/l sodium acetate buffer, pH 5.9. Unwanted protein and other impurities were flushed away with the equilibration buffer. Transferrin was eluted with 40 mmol/l Tris-HCl buffer, pH 7.5. The pH of the eluted, partly purified apotransferrin, was adjusted to pH 7.3 with the elution buffer. 1% (w/w) of Tween 80 and 0.3% (w/w) of tri-(n-butyl) phosphate were added, and the solution was treated at 26° C. for 10 h. The partly purified transferrin solution was applied to a chromatography column packed with Q Sepharose gel (Amersham Pharmacia, Sweden) pre-equilibrated with 40 mmol/l Tris-HCl buffer, pH 7.5. The solvent and detergent chemicals and protein impurities were flushed away with the equilibration buffer.

Apotransferrin was eluted using 40 mmol/l Tris-HCl buffer, pH 7.5, with 85 mmol/l sodium chloride.

The pH of the pure apotransferrin solution was adjusted to pH 6.0 using sodium acetate buffer, pH 4. The buffer was changed to 150 mmol/l sodium chloride, using diafiltration in an ultrafiltration unit. The solution was finally concentrated using the same equipment to a protein concentration of 55 g/l. The solution was prefiltered using a 0.1 µm filter (Gelman, Supor, USA) and virus filtered in tangential flow mode using a 15 nm virus filter (Asahi Industries, Japan) and the transferrin was recovered. The pure and virus-safe product was sterile filtered and aseptically filled into infusion bottles.

EXAMPLE 2

This Example describes the chemical and biochemical characteristics of the apotransferrin produced according to Example 1. The results of a typical product batch are shown in Table 1.

TABLE 1

Results of a transferrin batch produced according to the method described in Example 1

| Characteristic | Specification | Result |
| --- | --- | --- |
| Purity by SDS-PAGE (non-reduced) | Only transferrin bands visible | Only transferrin bands visible |
| Purity by cellulose acetate electrophoresis | >98% β-globulin | 99.7% β-globulin |
| Molecular size distribution by HPLC | >97% monomer <3% dimer (including immunoglobulins) 0% polymers or aggregates | 99% monomer 1% dimer (including immunoglobulins) 0% polymers or aggregates (FIG. 1) |
| Purity by urea-PAGE | Only apotransferrin band visible. After saturation with iron, complete change to diferric transferrin. | Only apotransferrin band visible. After saturation with iron, complete change to diferric transferrin (FIG. 2). |
| Iron binding capacity | >90% | 96% |
| Iron saturation | <5% | 0.8% |
| Prekallikrein activator | <1 IU/ml | <1 IU/ml |

EXAMPLE 3

This Example demonstrates how the pharmaceutical apotransferrin composition can be safely administered to patients to bind non-transferrin bound iron (NTBI) to a harmless form and prevent the harmful effects of NTBI in patients.

The pharmaceutical apotransferrin composition according to Example 2 was given to 6 patients, who had received allogeneic stem cell transplantation 3 days earlier and a preceding myeloablative treatment consisting of total body irradiation with 12 Gy and cyclofosfamide 120 mg/kg. All serum samples were positive for NTBI three days after the beginning of the high dose cytotoxic therapy, and NTBI typically remains positive up to 3 weeks in these patients. A single dose of apotransferrin (100 mg/kg) was given as an intravenous injection, which resulted in a rapid disappearance of NTBI in the serum samples of all patients. NTBI was determined by the bleomycin-detectable iron (BDI) assay, which is based on NTBI-induced degradation of DNA and measures free radical-generating activity of NTBI. The duration of the therapeutic effect of a single injection varied from 12 h to more than 12 days in the different patients.

Concomitantly with the disappearance of the radical-generating activity of NTBI, the growth of bacteria was prevented in the patients' serum samples after the administration of the transferrin composition. A multiresistant *Staphylococcus epidermidis* strain isolated from a septic infection, which did not grow in normal serum, grew in the serum samples of all patients before the administration of apotransferrin. The bacteria did not grow in any serum sample taken after transferrin administration, and started to grow slowly again in most serum samples taken 12 hours to 2 days after transferrin administration. In one patient, the growth inhibition lasted more than 12 days. As the *S. epidermidis* strain was resistant to other antibiotics than vancomycin, its growth in the serum samples was not affected by the chemotherapy received by the patients, when samples taken during vancomycin therapy were ruled out.

Figure 4:
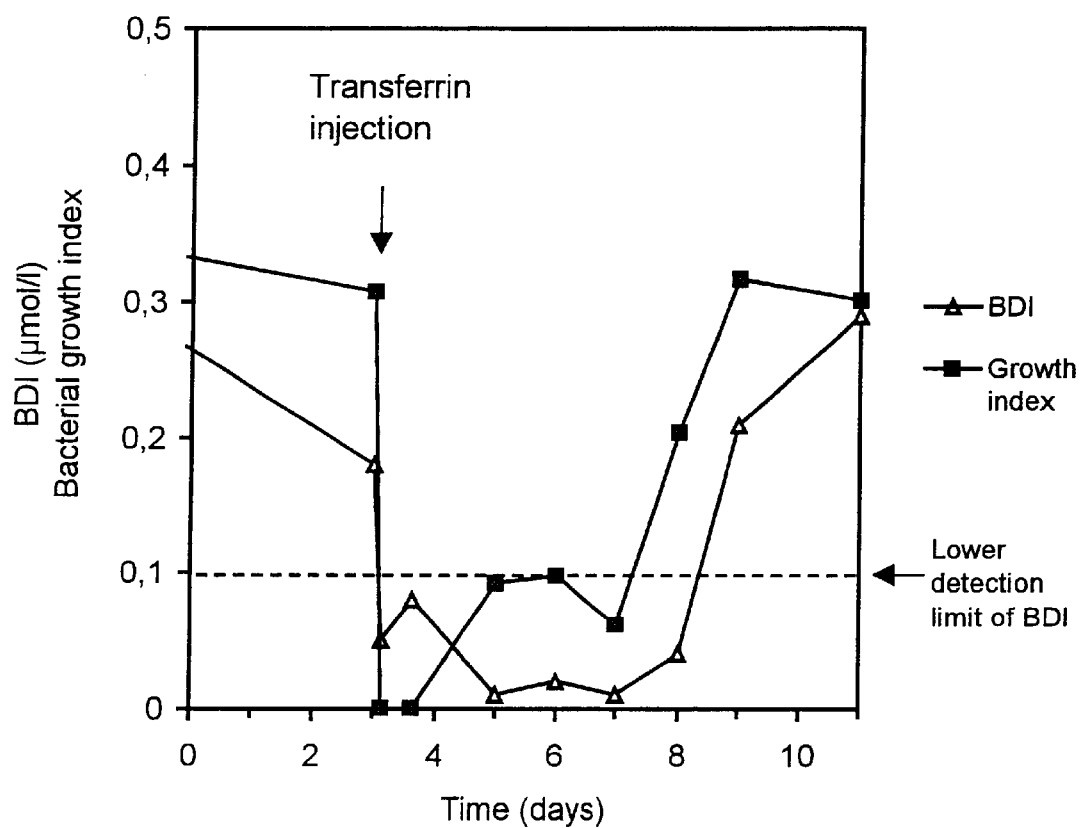
FIG. 4 shows the effects of a single injection (100 mg/kg) of a pharmaceutical apotransferrin composition according to the present invention on serum NTBI and bacterial growth in serum of a patient undergoing high dose cytotoxic therapy. Serum NTBI was determined by the bleomycin detectable iron (BDI) assay and bacterial growth with a multiresistant *Staphylococcus epidermidis* strain.

FIG. 4 shows the disappearance of NTBI (BDI assay) and inhibition of bacterial growth as a result of transferrin administration in one typical patient undergoing myeloablative therapy. FIG. 5 shows the growth curves for multiresistant *S. epidermidis* in serum samples of a patient before and after transferrin administration. The dependence of the observed effects in the patients on the administered apotransferrin composition was also demonstrated by adding the transferrin preparation in vitro to serum samples containing NTBI. The radical-generating activity as determined by the BDI assay was inhibited in a dose dependent manner when the apotransferrin preparation was added to the serum samples. Similarly, addition of the apotransferrn preparation inhibited effectively the growth of *S. epidermidis* and *Escherichia coli* strains in the serum samples.

The administration of the transferrin composition increased both serum transferrin and total serum iron concentration in all patients. The mean serum transferrin increased from 1.5 to 3.5 g/l and serum iron from 34 to 53 $\mu$mol/l. Determination of transferrin forms in the patients' serum samples by urea-PAGE indicated that the administered apotransferrin was converted to mono- and diferritransferrins. This indicates that the mechanism behind bacterial growth inhibition and disappearance of NTBI as a result of administration of the transferrin composition was the binding of NTBI to a harmless form and not a decrease of high serum iron level.

In another clinical condition, the pharmaceutical preparation was given to a newborn baby suffering from a lethal inborn error of metabolism, characterized by severe liver failure, low serum transferrin and very high concentration of NTBI in serum (Fellman et al., Lancet 351, 490–493, 1998). The administration of repeted doses of apotransferrin, on an average 200 mg/kg, removed transiently NTBI from serum., In the same patient, blood exchange did not significantly reduce the amount of NTBI in serum, thus emphasizing the efficacy of the pharmaceutic composition in the binding of NTBI.

No significant adverse effects related to the administration of the pharmaceutical apotransferrin composition were observed in careful monitoring of the patients receiving doses of 100–250 mg/kg of the composition. This indicated that the pharmaceutical apotransferrin composition of the present invention is well tolerated and can be safely administered even to critically ill patients.

What is claimed is:

1. Method for treating a patient suffering from a condition in which endogenous plasma transferrin is saturated with iron and there is non-transferrin-bound iron in the plasma, comprising administering an effective iron-binding amount of virus-safe apotransferrin having at least 90% of the theoretical iron binding capacity of iron-free transferrin, containing less than 3% transferrin dimers and no detectable transferrin polymers or aggregates and having an iron-saturation of less than 5%.

2. The method according to claim 1, wherein transferrin is administered to a patient undergoing a therapy selected from cytotoxic chemotherapy and cytotoxic radiation therapy.

3. The method according to claim 1, wherein transferrin is administered to a patient undergoing myeloablative therapy, and stem cell transplantation.

* * * * *